United States Patent
Kopperschmidt et al.

(10) Patent No.: US 9,233,341 B2
(45) Date of Patent: Jan. 12, 2016

(54) DEVICE AND METHOD FOR INSPECTING A FILTER FOR AN EXTRACORPOREAL BLOOD TREATMENT DEVICE

(75) Inventors: Pascal Kopperschmidt, Dittelbrunn (DE); Christoph Bocklet, Bad Bocklet (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 48 days.

(21) Appl. No.: 13/500,930

(22) PCT Filed: Oct. 1, 2010

(86) PCT No.: PCT/EP2010/006013
§ 371 (c)(1),
(2), (4) Date: Apr. 9, 2012

(87) PCT Pub. No.: WO2011/042137
PCT Pub. Date: Apr. 14, 2011

(65) Prior Publication Data
US 2012/0199526 A1 Aug. 9, 2012

(30) Foreign Application Priority Data
Oct. 10, 2009 (DE) .......................... 10 2009 048 920

(51) Int. Cl.
*B01D 61/00* (2006.01)
*B01D 35/00* (2006.01)
(Continued)

(52) U.S. Cl.
CPC ........... *B01D 65/102* (2013.01); *A61M 1/1656* (2013.01); *A61M 1/1672* (2014.02); *B01D 61/22* (2013.01); *A61M 2205/3317* (2013.01); *A61M 2205/705* (2013.01); *B01D 65/10* (2013.01);
(Continued)

(58) Field of Classification Search
None
See application file for complete search history.

(56) References Cited

U.S. PATENT DOCUMENTS 5,057,212 A 10/1991 Burrows
5,644,240 A 7/1997 Brugger
(Continued)

FOREIGN PATENT DOCUMENTS

EP 0 911 043 A1 4/1999
WO 2004/089440 A1 12/2004
WO 2006/026011 A1 3/2006

OTHER PUBLICATIONS

International Search Report from PCT/EP2010/005826 mailed on Jan. 20, 2011.

*Primary Examiner* — Nam Nguyen
*Assistant Examiner* — Richard Gurtowski
(74) *Attorney, Agent, or Firm* — Kenyon & Kenyon LLP

(57) ABSTRACT

The present invention relates to devices and methods for inspecting filters for extracorporeal blood treatment devices, e.g., filters for filtering dialysis fluid. The inspection of the filter according to the present invention is based on the measurement of the flow potential before and after changing the fluid flow of an electrolytic fluid between a transversal flow through the semi-permeable membrane of the filter and a longitudinal flow along the semi-permeable membrane of the filter, or vice versa. Changing the flow direction of the electrolytic fluid results in a change to the conductivity proceeding from a base value P to a higher value $P_2$ or a lower value $P_1$, wherein the conductivity readjusts to the base value P after a certain time interval $T_1$, $T_2$. An improper state of the filter is determined on the basis of the change in conductivity after changing the flow direction of the electrolytic fluid.

20 Claims, 3 Drawing Sheets

(51) Int. Cl.
*G01N 15/08* (2006.01)
*B01D 65/10* (2006.01)
*A61M 1/16* (2006.01)
*B01D 61/22* (2006.01)

(52) U.S. Cl.
CPC ......... *B01D 65/104* (2013.01); *B01D 2311/243* (2013.01)

(56) References Cited

U.S. PATENT DOCUMENTS

| | | |
|---|---|---|
| 5,779,911 A | 7/1998 | Haug et al. |
| 2006/0144765 A1* | 7/2006 | Skwiot ............................. 210/85 |
| 2006/0145658 A1* | 7/2006 | Wang ............................. 320/107 |
| 2006/0200064 A1* | 9/2006 | Gross et al. ................... 604/5.01 |

* cited by examiner

DEVICE AND METHOD FOR INSPECTING A FILTER FOR AN EXTRACORPOREAL BLOOD TREATMENT DEVICE

CROSS REFERENCE TO RELATED APPLICATIONS

This is a 371 national phase application of PCT/EP2010/006013 filed Oct. 1, 2010, which claims priority from German Patent Application No. 10 2009 048 920.7 filed Oct. 10, 2009.

FIELD OF INVENTION

The present invention relates to a device and a method for checking a filter for an extracorporeal blood treatment apparatus, in particular a filter for filtering dialyzing fluid for an extracorporeal blood treatment apparatus.

BACKGROUND OF THE INVENTION

Various methods for extracorporeal blood treatment are known. In hemodialysis (HD), the patient's blood is cleaned in an extracorporeal blood circuit which comprises a dialyzer. The dialyzer comprises a blood chamber and a dialyzing fluid chamber, which are separated by a semipermeable membrane.

Whereas dialyzing fluid flows through the dialyzing fluid chamber in the case of hemodialysis (HD), wherein specific substances are transported through the membrane due to diffusion between the dialyzing fluid and the blood, dialyzing fluid does not flow through the dialyzing fluid chamber of the dialyzer in the case of hemofiltration (HF). In the case of hemofiltration (HF), specific substances are effectively removed through the membrane of the filter due to convection. Hemodiafiltration (HDF) is a combination of the two methods.

It is generally known to replace a part of the fluid withdrawn from the patient via the membrane of the dialyzer or filter by a sterile substitution fluid (substituate), which is fed to the extracorporeal blood circuit upstream or downstream of the dialyzer. Apparatuses for extracorporeal blood treatment are known in which the dialyzing fluid is prepared online from fresh water and concentrate and the substituate is prepared online from the dialyzing fluid. The substituate is fed to the extracorporeal blood circuit from a dialyzing fluid system of the blood treatment apparatus via a substituate line upstream or downstream of the blood chamber of the dialyzer.

In order to avoid possible contamination of the dialyzing fluid with poisonous substances (pyrogens), the dialyzing fluid is filtered before it is fed to the blood circuit. For this purpose, the known blood treatment apparatuses comprise special pyrogen filters, which effectively retain decomposition products of bacteria and endotoxins in order to maintain a pyrogen-free dialysate (permeate).

The known blood treatment apparatuses generally comprise one or more pyrogen filters connected in series, which are disposed in the fluid system. The pyrogen filters have a similar structure to the dialyzer. Pyrogen filters are known which comprise a bundle of hollow fibers. Such pyrogen filters are referred to as capillary filters. The hollow-fiber bundle is disposed in a cylindrical housing in such a way that the openings of the individual fibers lie free at the end faces of the bundle. The capillaries in the hollow fibers form the primary side and the intermediate space between the hollow fibers forms the secondary side of the filter. The filtering takes place diffusively due to the pressure difference transversely to the fiber direction.

It is possible to subject pyrogen filters to an initial pressure test with compressed air. Here, the filter is closed downstream by a valve and an air overpressure is applied upstream and the pressure is monitored. If the pressure remains unchanged over a certain period of time, it can be assumed that there is an intact filter. If the pressure drops, it can thus be concluded that there are leaks in the fibers through which the compressed air can escape.

The known pyrogen filters have to be replaced after a certain time in service. The drawback is that, in practice, the replacement intervals for pyrogen filters have to be rigidly preselected irrespective of the actual state of the filter. In practice, therefore, the filters may in principle be changed too soon or too late.

US 2008/0203023 A1 describes a blood treatment apparatus, which comprises a pyrogen filter which comprises an integrated conductivity sensor, in order to monitor the quality of the dialyzing fluid flowing through the filter. This alone does not however allow information to be provided as to the state of the filter.

WO 2008/089913 A2 describes a blood treatment apparatus, which comprises a device for establishing the calcification of a pyrogen filter. This device comprises sensors which are disposed upstream and downstream of the filter. The sensors measure the conductivity of the dialyzing fluid flowing continuously through the semipermeable membrane of the filter.

DE 198 32 451 C1 describes a device for checking the correctly implemented replacement of a used filter in an apparatus for extracorporeal blood treatment. The checking of the correctly implemented filter replacement takes place by means of a pressure-holding test, wherein it is concluded, in the case of permeability of the filter membrane for a gas, that the used filter has been replaced by a new filter.

SUMMARY OF THE INVENTION

The problem underlying the present invention is to provide a device for checking a filter for an extracorporeal blood treatment apparatus, in particular a filter for filtering dialyzing fluid, with which the correctly functioning state of the filter can be reliably ascertained. A further problem of the present invention is to make available an extracorporeal blood treatment apparatus with such a device and to specify a method for checking a filter.

The device according to the present invention and the method according to the present invention for checking a filter are based on the measurement of the flow potential before and after the change of the fluid flow of an electrolytic fluid, in particular permeate (ultra-pure water) or dialyzing fluid, between a transverse flow through the semipermeable membrane of the filter and a longitudinal flow along the semipermeable membrane of the filter. Alternatively, however, it is also possible to measure the flow potential of the electrolytic fluid before and after the change between a longitudinal flow along the semipermeable membrane of the filter and a transverse flow through the semipermeable membrane of the filter. In principle, it is also possible to measure the conductivities both during a transfer from a transverse to a longitudinal flow as well as during a transfer from a longitudinal flow to a transverse flow.

The acquisition of the flow potential by means of a conductivity measurement permits the noninvasive checking of the integrity of a filter, in particular a pyrogen filter. As a result of the filter being used, its endotoxin retention rate changes due to a changed permeability of the filter pores. This leads to a change in the magnitude of the flow potential. The magnitude of the flow potential also depends on the electrolyte concentration, the type of electrolyte, the flow rate, the surface polarity and the geometry of the pores of the filter.

After the change of the flow direction of the electrolytic fluid, a change arises in the conductivity after the filter in the transverse and longitudinal direction, proceeding from a base value to a higher value or a lower value, the conductivity again returning to the base value after a specific time interval. An incorrectly functioning state of the filter is ascertained on the basis of the change in the conductivity after the change in the flow direction of the electrolytic fluid.

In order to perform the measurement procedure, the device according to the present invention comprises means for generating a change in the flow direction from a transverse to a longitudinal and from a longitudinal to a transverse flow. Such means can comprise fluid lines and shut-off elements known to the person skilled in the art, with which the electrolytic fluid is conveyed along the membrane or through the membrane. Moreover, the device according to the present invention comprises a computing and evaluation unit for monitoring the change in conductivity after the change in the flow direction of the electrolytic fluid, said unit being designed such that an incorrectly functioning state of the filter is ascertained on the basis of the change in the conductivity after the change in the flow direction of the electrolytic fluid.

The means for measuring the conductivity can comprise a conductivity sensor which is disposed downstream of the filter on the primary side, or can comprise a conductivity sensor which is disposed downstream of the filter on the secondary side of the filter. Here, the primary side of the filter comprises the interior of the hollow fibers, to which the fluid supply is connected, the secondary side comprising the region between the dialyzer housing and the hollow fibers, in which region the fluid filtered through the pores of the hollow fibers collects. It is however also possible for two sensors to be provided, one whereof is disposed on the primary side and the other on the secondary side. Instead of two sensors for acquiring the conductivity both on the primary and the secondary side, it is also possible to provide only a single conductivity sensor if the electrolytic fluid for both measurements is fed to the single conductivity sensor via an arrangement of fluid lines and shut-off elements known to the person skilled in the art.

A preferred embodiment of the present invention makes provision, after a change in the flow direction from a transverse flow to a longitudinal flow, to ascertain the amount of the increase in the conductivity of the electrolytic fluid after the filter in the longitudinal direction from a base value to a maximum value, i.e., to detect the size of the jump in conductivity to be detected. The size of the jump in conductivity depends on the base conductivity of the electrolyte and on the polarity of the membrane. The amount of the increase in conductivity is compared with a preselected threshold value, an incorrectly functioning state of the filter being ascertained if the amount is less than the preselected threshold value.

An alternative embodiment makes provision to monitor a change in the conductivity of the electrolytic fluid after the filter in the transverse direction after a change from a longitudinal flow to a transverse flow. In this case, a drop in the conductivity can be detected from the base value to a minimum value by a specific amount. The size of the drop in conductivity depends on the base conductivity of the electrolyte and on the polarization of the membrane. The amount of the drop in conductivity is compared with a preselected threshold value, an incorrectly functioning state of the filter being ascertained if the amount is less than the preselected threshold value. In principle, it is also possible to combine the two alternative embodiments with one another, the ascertained measurement values being evaluated statistically using methods known to the person skilled in the art.

Another alternative embodiment provides for the determination of the integral over time of the changes in conductivity, instead of ascertaining the amount of the changes in conductivity from a base value. It emerges that the integral of the jump in conductivity with a change from a transverse to a longitudinal flow is, for reasons of charge-retention, equal to the integral of the drop in conductivity with a change from a longitudinal flow to a transverse flow.

It has been shown that the magnitude of the change in conductivity, or its integral over time, diminishes if the pores of the semipermeable membrane of the filter become clogged up with increasing time in use. The maximum permissible service life of the filter can thus be stipulated with a specific threshold value. If the amount of the change in conductivity or its integral over time is less than the preselected threshold value, the filter must be replaced. The preselected threshold value can be stored in a memory of the computing and evaluation unit. The threshold value can be determined empirically using comparative measurements. It is possible to fix the threshold value when a new filter is used, the threshold value then being a specific percentage proportion of the amount of the increase in conductivity that is measured with the new filter.

With the method according to the present invention and the device according to the present invention, it is possible not only to ascertain when the filter has to be replaced, but it is also possible to ascertain whether, in an extracorporeal blood treatment apparatus, a dummy filter is being used that serves solely to short-circuit the fluid lines, but does not have a filtering effect. It is concluded that a dummy filter is being used when a change in conductivity cannot be detected.

Moreover, it is possible to check the integrity of the capillaries of the semipermeable membrane of the filter using the device according to the present invention and the method according to the present invention. It can be concluded that there are tears or defects in the semipermeable membrane when a significant jump in conductivity cannot be detected after the change of the flow direction.

If a plurality of filters are present in the extracorporeal blood treatment apparatus for filtering the dialyzing fluid, all the filters can be checked for a correctly functioning state using the device according to the present invention and the method according to the present invention. It is also possible to compare with one another the changes in conductivity that arise with the two filters, in order to be able to provide information as to the state of one filter compared to the state of the other filter.

BRIEF DESCRIPTION OF THE DRAWINGS

A number of examples of embodiment of the present invention are explained in greater detail below by reference to the drawings.

In the figures.

DETAILED DESCRIPTION OF THE DRAWINGS

Figure 1:
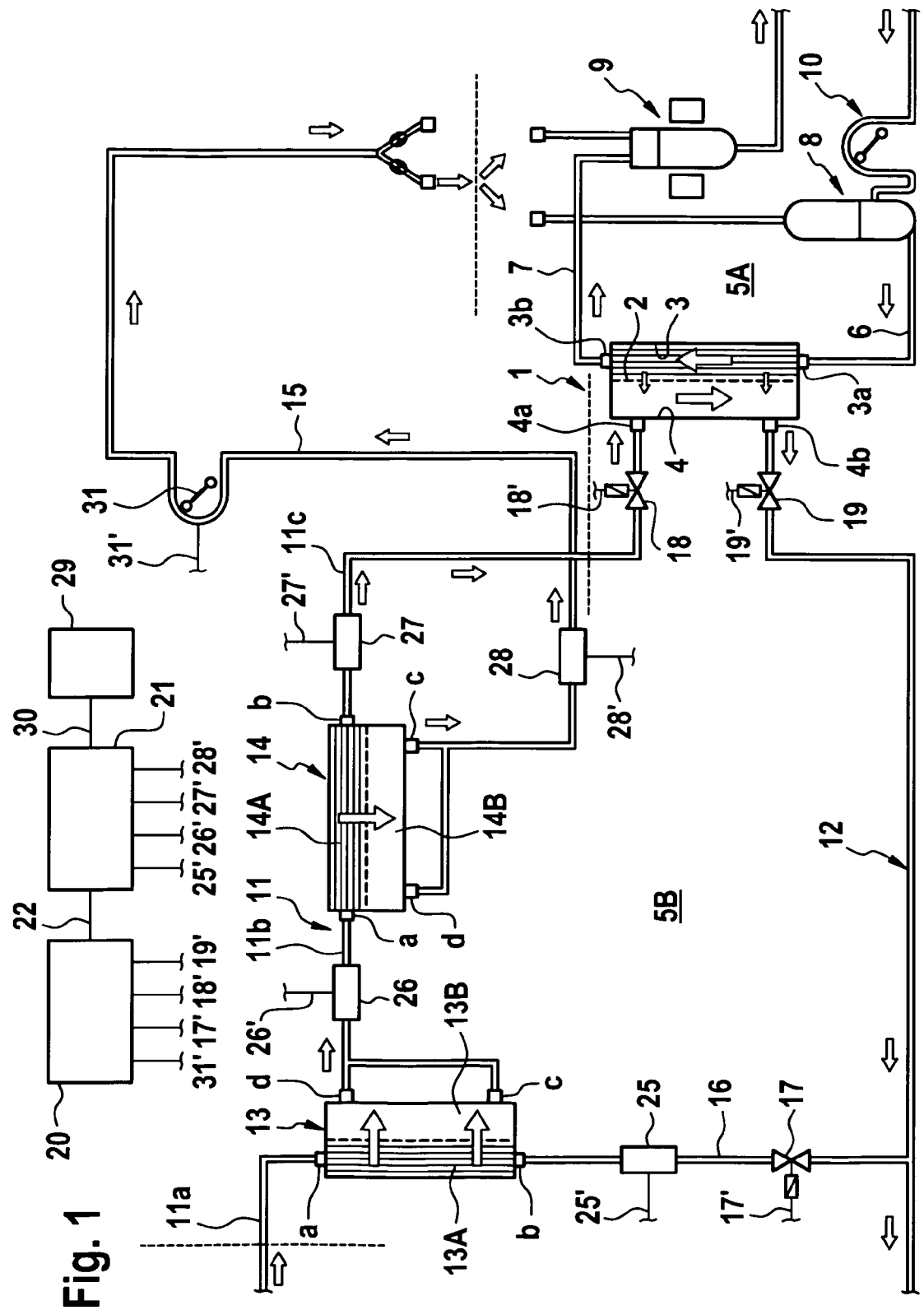
FIG. 1 shows the main components of an apparatus for extracorporeal blood treatment with a device for checking the filters for filtering the dialyzing fluid in a very simplified schematic representation.

FIG. 1 shows a simplified schematic representation of the main components of an extracorporeal blood treatment apparatus, in particular a hemo(dia)filtration apparatus, which comprises a device for checking the filters present in the blood treatment apparatus for filtering the dialyzing fluid.

The hemo(dia)filtration apparatus comprises a dialyzer 1, which is divided by a semipermeable membrane 2 into a first chamber 3 through which blood flows and a second chamber 4 through which dialyzing fluid flows. First chamber 3 is incorporated in an extracorporeal blood circuit 5A, while the second chamber is incorporated in fluid system 5B of the hemo(dia)filtration apparatus.

Extracorporeal blood circuit 5A comprises an arterial blood line 6 which leads to inlet 3*a* of blood chamber 3 and a venous blood line 7 which leads away from outlet 3*b* of the blood chamber of dialyzer 1. In the present example of embodiment, an arterial drip chamber 8 is incorporated in arterial blood line 6 and a venous drip chamber 9 in venous blood line 7 in order to eliminate air bubbles. The blood is conveyed in the extracorporeal circuit by means of a blood pump 10, which is disposed in arterial blood line 6.

Fluid system 5B comprises a dialyzing fluid supply line 11, which leads to inlet 4*a* of dialyzing fluid chamber 4, and a dialyzing fluid discharge line 12, which leads away from outlet 4*b* of dialyzing fluid chamber 4 of dialyzer 1. Fresh dialyzing fluid flows via dialyzing fluid supply line 11 out of a dialyzing fluid source (not shown) into dialyzing fluid chamber 4, while used dialyzing fluid is carried away from the dialyzing fluid chamber via dialyzing fluid discharge line 12 to a drain (not shown). The dialyzing fluid is conveyed in fluid system 5B by means of a dialyzing fluid pump (not shown).

During the blood treatment, a sterile substitution fluid (substituate) can be obtained from the dialyzing fluid in fluid system 5B and fed to extracorporeal blood circuit 5A. Two sterile filters 13, 14 (pyrogen filters), which are disposed in fluid system 5B, are used to obtain sterile dialyzing fluid. Both sterile filters are capillary filters, the semipermeable membrane whereof is formed by a bundle of hollow fibers.

Figure 3:
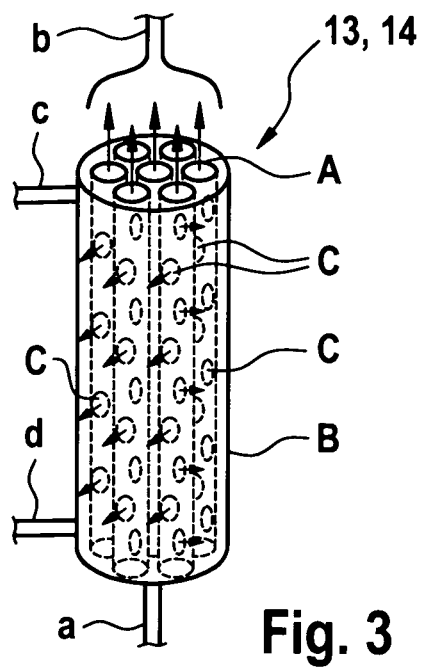
FIG. 3 shows the structure of a capillary filter for filtering dialyzing fluid and FIG. 4 shows the change in the conductivity with the number of degreasing cycles of a pyrogen filter.

FIG. 3 shows the structure of one of the two sterile filters 13, 14 (pyrogen filters) in a very simplified schematic representation. Hollow-fiber bundle A is disposed in a cylindrical housing B in such a way that the openings of the individual fibers lie free at the end faces of the housing. Two connections a and b of the first chamber (primary side) of the filter are located at the openings of the capillaries on the end faces of the housing, while two outlets c and d of the second chamber (secondary side) of the filter are located at the upper and lower end of the housing wall. When a pressure difference is present between the primary side and secondary side, an exchange takes place through pores C of hollow-fiber bundle A. The flow direction through the pores of the capillaries of hollow-fiber bundle A in the transverse direction and along the capillaries in the longitudinal direction is marked by arrows in FIG. 3.

The two sterile filters 13, 14 are incorporated in series in fluid system 5B. A first segment 11*a* of dialyzing fluid supply line 11 leads to first inlet a of first chamber 13A of first sterile filter 13. A second segment 11*b* of dialyzing fluid supply line 11 leads away from two outlets c, d of second chamber 13B of first sterile filter 13 and leads to an inlet a of first chamber 14A of second sterile filter 14. A third segment 11*c* of dialyzing fluid line 11 leads away from second inlet b of first chamber 14A of second sterile filter 14 and leads to inlet 4*a* of dialyzing fluid chamber 4 of dialyzer 1.

The sterile dialyzing fluid is removed from second chamber 14B of second sterile filter 14. Leading away from two outlets c, d of second chamber 14B of second sterile filter 14 is a substituate line 15, which leads to extracorporeal blood circuit 5A. Substituate line 15 can be connected either to arterial drip chamber 8 or venous drip chamber 9, in order to supply the substitution fluid upstream or downstream of dialyzer 1. The substituate is conveyed by means of a substituate pump 31.

Fluid system 58 makes provision such that both sterile filters 13, 14 are operated in such a way that the dialyzing fluid flows through the semipermeable membrane of the filters or the dialyzing fluid flows along the membrane. The flow direction through the membrane is denoted as a transverse flow and the flow direction along the membrane as a longitudinal flow.

In order to be able to operate the first sterile filter in the through-flow, a rinsing line 16 leads away from second inlet b of first chamber 13A of sterile filter 13, said rinsing line leading to dialyzing fluid return line 12. Located in rinsing line 16 is an electromagnetically or pneumatically operated shut-off element 17. Further shut-off elements 18, 19 are located in dialyzing fluid supply line 11 between second sterile filter 14 and dialyzing fluid chamber 4 of dialyzer 1 and downstream of the dialyzer in dialyzing fluid return line 12.

The control of the blood treatment apparatus takes place with a central control unit 20, which is connected by control lines to the individual components of the blood treatment apparatus. FIG. 3 shows only control lines 31', 17', 18' and 19' for substituate pump 31 and shut-off elements 17, 18 and 19.

The extracorporeal blood treatment apparatus comprises a device for checking both sterile filters 13, 14. The device for checking the sterile filters can be a component of the blood treatment apparatus or a separate device. In the present example of embodiment, the device is a component of the blood treatment apparatus. The device can therefore make use of components which are already present in the blood treatment apparatus.

The device for monitoring the sterile filters comprises a computing and evaluation unit 21, which is connected by a data line 22 to central control unit 20. Computing and evaluation unit 21 can however also be a component of control unit 20. Moreover, the device comprises a plurality of conductivity sensors 25, 26, 27 and 28, whereof first conductivity sensor 25 is disposed in rinsing line 16 upstream of shut-off element 17, second conductivity sensor 26 is disposed in second segment 11*b* of dialyzing fluid supply line 11 between first and second sterile filters 13, 14, third conductivity sensor 27 is disposed in third segment 11*c* of dialyzing fluid supply line 11 between second sterile filter 14 and dialyzing fluid chamber 4 of dialyzer 1 and third conductivity sensor 28 is disposed in substituate line 15 upstream of substituate pump 31. Conductivity sensors 25, 26, 27 and 28 are connected by data lines 25', 26', 27' and 28' to computing and evaluation unit 21. Furthermore, the device comprises a signal unit 29, which is connected by a data line 30 to computing and evaluation unit 21.

The mode of functioning of the device for monitoring the sterile filters is described in detail below.

The flow direction in the sterile filters to be checked is changed over in order to check the sterile filters. It is possible to change over the flow direction from a transverse flow to a longitudinal flow or from a longitudinal flow to a transverse flow. The flow direction is preferably changed over periodically during testing.

In order to check first sterile filter 13, the change-over of the flow direction takes place as follows. For a transverse flow, control unit 20 closes shut-off element 17 in rinsing line 16. The conductivity of the dialyzing fluid downstream of first sterile filter 13 is measured with conductivity sensor 26 in second segment 11*b* of dialyzing fluid supply line 11. In order to generate a longitudinal flow, control unit 20 opens shut-off element 17 in rinsing line 16, the conductivity of the dialyzing fluid being measured with conductivity sensor 25 in rinsing line 16.

In order to check second sterile filter 14, the change-over of the flow direction takes place as follows. Control unit 20 stops substitute pump 31 in order to generate a longitudinal flow, shutoff element 18 being opened in third line segment 11*c* of dialyzing fluid supply line 11. The dialyzing fluid thus flows through first chamber 14A of second sterile filter 14, the conductivity of the dialyzing fluid (substitute) being measured downstream of sterile filter 14 with conductivity sensor 27, which is disposed in third segment 11*c* of dialyzing fluid supply line 11.

In order to generate a transverse flow, control unit 20 closes shut-off element 18 and puts substitute pump 31 into operation. The conductivity of the dialyzing fluid is measured with conductivity sensor 28 in substitute line 15.

Figure 2:
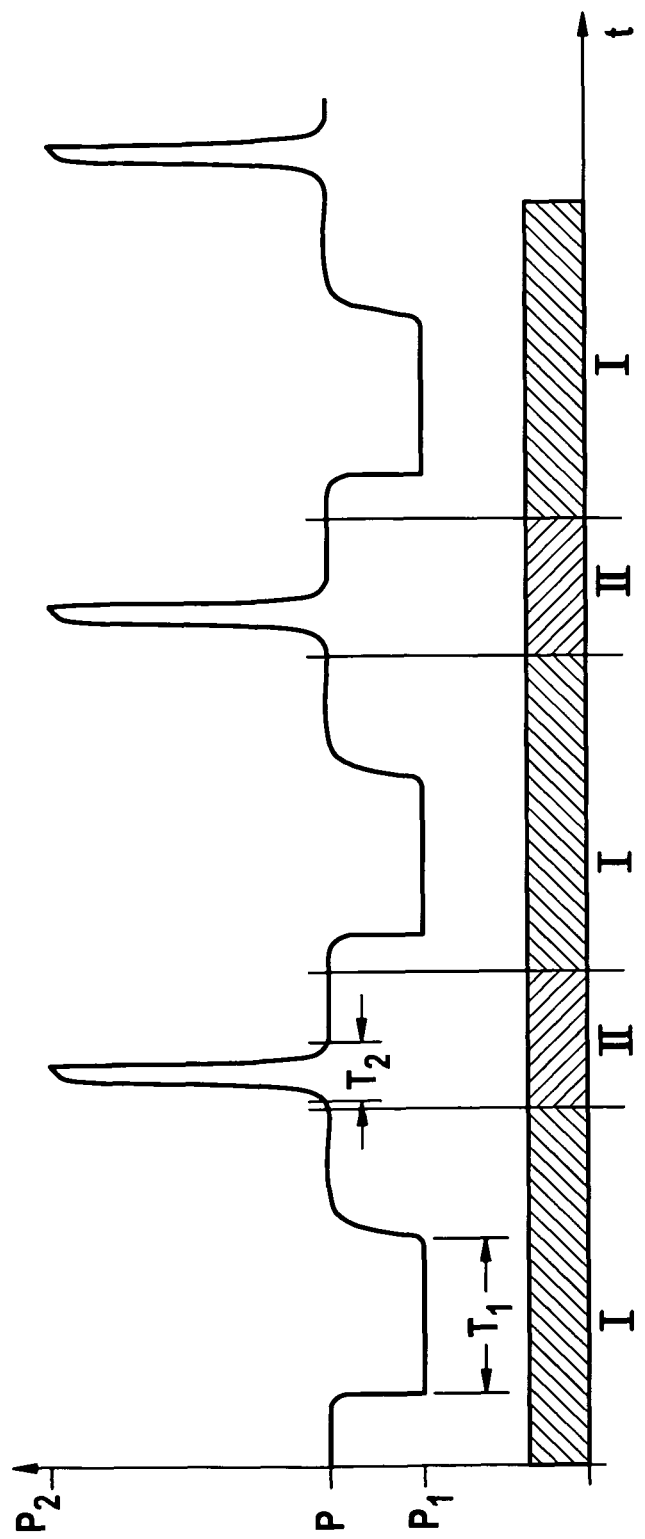
FIG. 2 shows the change in the conductivity of the dialyzing fluid downstream of the filter after a change in the flow direction between a transverse and a longitudinal flow and a longitudinal and transverse flow.

FIG. 2 shows the conductivity values as a function of time t measured with the two conductivity sensors 25, 26 and 27, 28 respectively, the flow direction being changed periodically from a transverse flow I to a longitudinal flow II. FIG. 2 serves merely to illustrate the change in conductivity with the periodic reversal of the flow direction through one of the two filters 13, 14. Depending on the state of the two filters, different conductivity values result in practice.

It emerges that, after a reversal of the flow direction from a longitudinal flow II to a transverse flow I, the conductivity falls from a base value P to a minimum value $P_1$ within a specific time interval $T_1$, then increasing again to base value P. With a change from a transverse flow I to a longitudinal flow II, the conductivity increases from a base value P to a maximum value $P_2$ within a preset time interval $T_2$, then falling again to base value P. A conductivity increase and a conductivity decrease can thus be detected, which can be traced back to the fact that charge carriers in the electrolytic fluid (dialyzing fluid) are released for a short time. The shift in conductivity amounts to approx. 1-5 μS/cm in the case of a base conductivity of approx. 7 μS/cm typical of permeate.

The device according to the present invention permits the checking of all filters comprising polar surfaces. This is the case, for example, with polysulfone filters. If the electrolytic fluid, which in the present example of embodiment is a dialyzing fluid, passes through the pores of the membrane (transverse flow), the negative ions (Co ions) become enriched at the polar surface of the hollow fibers of the polysulfone filter and pull positive ions of the dialyzing fluid in the direction of the surface of the capillaries. This process takes place not only at the pores of the capillaries, but also at the whole surface of the polysulfone filter. The inner walls of the pores are therefore occupied by positive ions of the dialyzing fluid, which for their part generate a counter-field which subsequently cancels out the attracting effect of the Co ions, so that the fields become neutralized. A saturation thus arises, after which no further positive ions of the dialyzing fluid adhere to the surface of the capillaries. Since the charge carriers are stopped, the conductivity of the fluid diminishes downstream of the filter. As a result of the saturation, the conductivity then increases again to the original value (base value). Finally, the conductivity of fresh dialyzing fluid is measured without the removal of charge carriers.

When the electrolytic fluid flows along the membrane of the filter, the pores of the capillaries are rinsed. As a result, the positive ions of the electrolytic fluid, for example the dialyzing fluid, now move normal to the previous direction through the capillaries. As a result, the Co ions in the pores are moved in the direction of the fluid flow towards the inner wall of the capillaries and carry the adhering positive ions out of the pores back into the capillaries. The dialyzing fluid thus receives a "charge carrier bolus" which can be detected as a short-time conductivity increase downstream of the filter in the longitudinal direction. Once this charge carrier bolus has passed the conductivity sensor, dialyzing fluid with the base conductivity again flows past the conductivity sensor.

The amount of the increase or decrease in conductivity depends decisively on the size of the pores of the capillaries and on the conductivity of the electrolytic fluid. The size of the pores determines how many charge carriers can be retained in relation to the through-flowing fluid. If the pores are very large, the number of retained charge carriers is of no consequence in relation to the large through-flow through the large diameter pores. In practice, however, the pores of the capillaries of the employed sterile filters have a size such that the conductivity increase or decrease can be measured with sufficient accuracy.

It has been shown that the jump in conductivity after the change of the flow direction in the filter diminishes with increasing age of the filter. A check can therefore be made to establish whether the filter needs to be replaced.

In a first example of embodiment, computing and evaluation unit 21 of the device for checking one of the two or both filters 13, 14 of the blood treatment apparatus measures the amount of conductivity by which the conductivity falls from base value P to minimum value $P_1$ within preset time interval $T_1$. Computing and evaluation unit 21 compares this value with a preselected threshold value. If the amount of the drop in conductivity is less than the threshold value, computing and evaluation unit 21 concludes that the filter needs to be replaced. The computing and evaluation unit then generates a signal which is received by signal unit 29. A prompt to replace the filter is then signaled by signal unit 29, which can emit an acoustic and/or optical and/or tactile alarm.

The preselected threshold value for evaluating the age of the filter can be checked by a reference measurement with a new filter. In one example of embodiment of the present invention, the monitoring device itself carries out the reference measurement for determining the threshold value after the replacement of an old filter by a new one, the threshold value then being a specific percentage proportion of the amount of the increase in conductivity that is measured with the new filter. This reference value is stored in a memory of computing and evaluation unit 21. In the subsequent treatments, the measured conductivity values are then compared with the stored threshold value. It is also possible to ascertain the threshold value empirically on the basis of a measurement with a used filter, it being assumed that the used filter has just reached its maximum useful life.

Another embodiment of the present invention makes provision not to measure the negative jump in conductivity after a change in the flow direction from a longitudinal to a transverse flow, but to carry out the measurement of the amount of the jump in conductivity from a base value P to a maximum value $P_2$ after a change from a transverse to a longitudinal flow. In this example of embodiment, the amount of the increase in conductivity is compared with a preselected threshold value. It is however also possible to combine both measurements together, which can be ascertained according to the threshold value before the drop in conductivity.

In an alternative embodiment, it is not the amount of the increase or decrease in conductivity, but rather the integral of the jump in conductivity that is calculated by computing and evaluation unit 21. The integral of the jump in conductivity corresponds, in relation to the base value, to the area under the curve in time interval $T_1$ and $T_2$. With this example of embodiment, computing and evaluation unit 21 compares the integral of the jump in conductivity with a preselected threshold value, which is ascertained as in the first example of embodiment and stored in the memory of the computing and evaluation unit.

In the event that computing and evaluation unit 21 does not detect the jump in conductivity, it is concluded that there is a possible defect in the filter. It has been shown that, in the case of cracks in the capillaries of the filter, the through-flow is so great that the retained ions have no effect on the conductivity. The possible defect in the filter is again signaled by signal unit 29.

With the measurement of the conductivity, computing and evaluation unit 21 is also able to check whether a filter for filtering dialyzing fluid or only a dummy filter is being used in the blood treatment apparatus, serving solely to produce a fluid connection between the connections of the dialyzing fluid lines. In the event that computing and evaluation unit 21 does not detect a jump in conductivity, signal unit 29 signals that a dummy filter has possibly been fitted.

In another example of embodiment of the present invention, measurements are carried out respectively for first and second sterile filters 13, 14. The amount of the jump in conductivity or the integral of the jump in conductivity of the one filter is then compared by the evaluation unit with the amount or the integral of the jump in conductivity of the other filter. If the difference in the conductivity jumps of the two filters exceeds a preselected threshold value, it is concluded that there are differing degrees of wear or possible defects in one of the two filters. This measurement result can again be signaled by the signal unit.

When checking filters of a hemo(dia)filtration apparatus, it is recommended to use, as an electrolytic fluid, the permeate which in any case flows through the fluid system. The measurement is advantageously carried out before the dialysis treatment. In principle, however, a measurement during the dialysis is also possible if the extracorporeal blood circuit is separated from the vascular blood circuit by means of an arterial or venous clamp for the period of the measurement. The measurement can take place during the rinsing process in the machine before the actual dialysis treatment. The measurement before the dialysis treatment has the advantage that the base conductivity of the dialyzing fluid (rinsing fluid) can be changed without regard to the patient. It has been shown that typical base conductivities are advantageous for different filters, since they lead to a particularly large jump in conductivity. During the dialysis, the base conductivity can also be varied within certain limits when the vascular blood circuit is decoupled from the extracorporeal blood circuit. Then, however, the solution, which possibly presents a health hazard to the patient, must first be removed again from the fluid system, the fluid system having to be rinsed again and the fluid discarded.

It has been shown that, when the dialysis machine is disinfected and degreased with hypochlorite, the electrochemical properties of the surface of the pyrogen filter are changed in such a way that they intensify the effect of the shift in conductivity.

Figure 4:
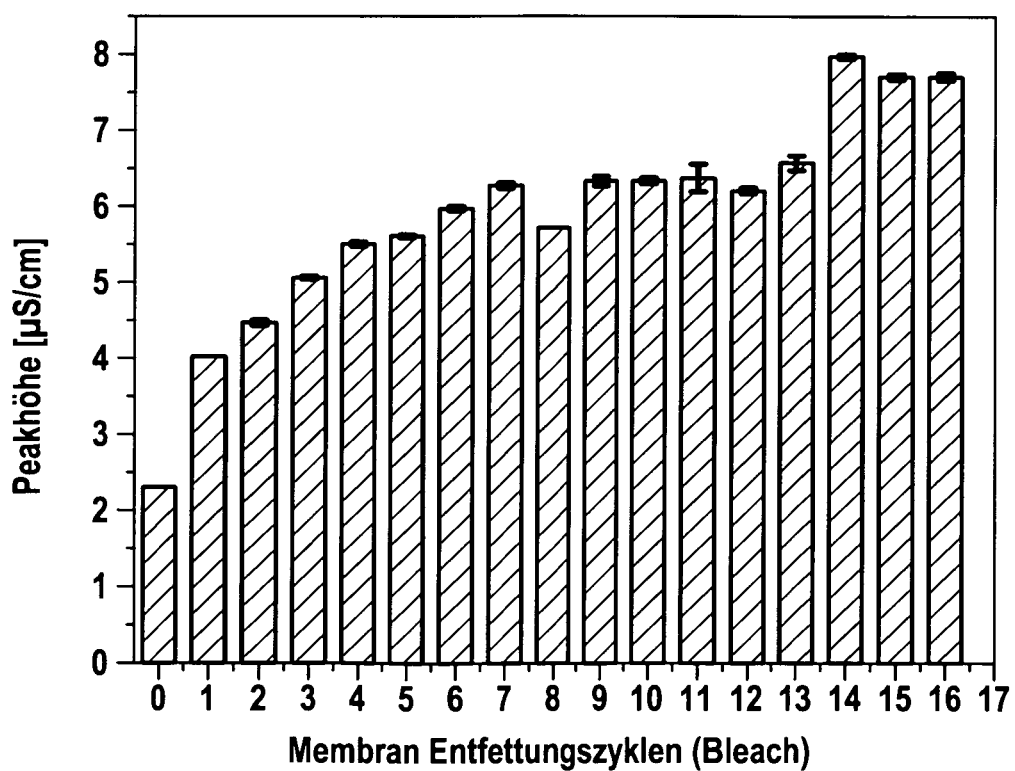

FIG. 4 shows the influence that rinsing with hypochlorite for disinfection of the machine has on the electrical-polar properties of the PVP-polysulfane membrane. Hypochlorite washes the PVP (polyvinyl pyrrolidone) out of the membrane. The membrane thus becomes polar, as a result of which the effect of the shift in conductivity is intensified. In practice, however, the rinsing of a machine with hypochlorite takes place only very seldom, typically one or two times per year. The shift in conductivity as a result of disinfecting the machine with hypochlorite can be duly taken into account when selecting the threshold value.

On the other hand, the disinfection of the blood treatment apparatus with a temperature-regulated disinfectant, for example a citrate solution, does not have any influence on the magnitude of the shift in conductivity.

What is claimed is:

1. A device for checking a filter having a semipermeable membrane which separates a primary side and a secondary side of the filter, the device comprising:
   a flow direction changing system configured to generate:
      a change in a flow direction between a transverse flow of an electrolytic fluid through the semipermeable membrane of the filter and a longitudinal flow of the electrolytic fluid along the semipermeable membrane of the filter; and
      a change between the longitudinal flow of the electrolytic fluid along the semipermeable membrane of the filter and the transverse flow of the electrolytic fluid through the semipermeable membrane of the filter;
   a measurement system arranged downstream of the filter and configured to measure a conductivity of the electrolytic fluid flowing in the transverse direction downstream of the filter and of the electrolytic fluid flowing in the longitudinal direction downstream of the filter; and
   a computing and evaluation unit configured to monitor a change in the conductivity after the change in the flow direction of the electrolytic fluid from a base value, said unit being configured such that a presence of an incorrectly functioning state of the filter is ascertained based on the change in the conductivity after the change in the flow direction of the electrolytic fluid.

2. The device according to claim 1, wherein the computing and evaluation unit is configured such that after a change in the flow direction of an electrolytic fluid between a transverse flow through a semipermeable membrane of the filter and a longitudinal flow of the electrolytic fluid along the semipermeable membrane of the filter, an amount of the change in conductivity from a base value is determined and compared with a preselected threshold value, an incorrectly functioning state of the filter being ascertained if the amount is less than the preselected threshold value.

3. The device according to claim 1, wherein the computing and evaluation unit is configured such that after a change in the flow direction of an electrolytic fluid between a longitudinal flow along the semipermeable membrane of the filter and a transverse flow of the electrolytic fluid through the semipermeable membrane of the filter, an amount of the change in conductivity from a base value is determined and compared with a preselected threshold value, an incorrectly functioning state of the filter being ascertained if the amount is less than the preselected threshold value.

4. The device according to claim 1, wherein the computing and evaluation unit is configured such that after a change in the flow direction of an electrolytic fluid between a transverse flow through the semipermeable membrane of the filter and a longitudinal flow of the electrolytic fluid along the semipermeable membrane of the filter, an integral of the change in conductivity is determined and compared with a preselected threshold value, an incorrectly functioning state of the filter being ascertained if the integral is less than the preselected threshold value.

5. The device according to claim 1, wherein the computing and evaluation unit is configured such that after a change between a longitudinal flow of an electrolytic fluid along the semipermeable membrane of the filter and a transverse flow of the electrolytic fluid through the semipermeable membrane of the filter, an integral of the change in conductivity is determined and compared with a preselected threshold value, an incorrectly functioning state of the filter being ascertained if the integral is less than the preselected threshold value.

6. The device according to claim 2, wherein the computing and evaluation unit is configured such that an incorrectly functioning state of the filter is ascertained if it is determined that there is no change in the conductivity from the base value.

7. The device according to claim 1, wherein the electrolytic fluid is dialyzing fluid or permeate.

8. The device according to claim 1, wherein the filter is a capillary filter which comprises a bundle of hollow fibers.

9. The device according to claim 1, wherein the filter is a filter for filtering dialyzing fluid for an extracorporeal blood treatment apparatus.

10. An apparatus for extracorporeal blood treatment comprising:
an extracorporeal blood circuit;
a dialyzer having a first chamber and a second chamber divided by a semipermeable membrane;
a dialyzing fluid system which includes the second chamber of the dialyzer, wherein a substitute line leads from the dialyzing fluid system to the blood circuit and at least one filter for filtering dialyzing fluid is disposed in the dialyzing fluid system; and
a device according to claim 1 for checking the at least one filter for filtering dialyzing fluid, said filter being disposed in the dialyzing fluid system.

11. The device according to claim 10, wherein the device comprises a signal unit which cooperates with the computing and evaluation unit and emits a signal when an incorrectly functioning state of the filter is ascertained by the computing and evaluation unit.

12. A method for checking a filter having a semipermeable membrane which separates a primary side and a secondary side of the filter from one another, the method comprising the following process steps:
generating:
a change in a flow direction between a transverse flow of an electrolytic fluid through the semipermeable membrane of the filter and a longitudinal flow of the electrolytic fluid along the semipermeable membrane of the filter; and
a change between the longitudinal flow of the electrolytic fluid along the semipermeable membrane of the filter and the transverse flow of the electrolytic fluid through the semipermeable membrane of the filter;
measuring a conductivity of the electrolytic fluid flowing in the transverse direction downstream of the filter and of the electrolytic fluid flowing in the longitudinal direction downstream of the filter;
monitoring a change in the conductivity after the change in the flow direction of the electrolytic fluid from a base value; and
concluding that there is an incorrectly functioning state of the filter based on the change in the conductivity after the change in the flow direction of the electrolytic fluid.

13. The method according to claim 12, wherein after a change in the flow direction of an electrolytic fluid between a transverse flow through the semipermeable membrane of the filter and a longitudinal flow of the electrolytic fluid along the semipermeable membrane of the filter, an amount of the change in conductivity from a base value is determined and compared with a preselected threshold value, it being ascertained that there is an incorrectly functioning state of the filter if the amount is less than the preselected threshold value.

14. The method according to claim 12, wherein after a change in the flow direction between a longitudinal flow of an electrolytic fluid along the semipermeable membrane of the filter and a transverse flow of the electrolytic fluid through the semipermeable membrane of the filter, an amount of the change in conductivity from a base value is determined and compared with a preselected threshold value, it being ascertained that there is an incorrectly functioning state of the filter if the amount is less than the preselected threshold value.

15. The method according to claim 12, wherein after a change in the flow direction between a transverse flow of an electrolytic fluid through the semipermeable membrane of the filter and a longitudinal flow of the electrolytic fluid along the semipermeable membrane of the filter, an integral of the change in conductivity is determined and compared with a preselected threshold value, it being ascertained that there is an incorrectly functioning state of the filter if the integral is less than the preselected threshold value.

16. The method according to claim 12, wherein after a change in the flow direction between a longitudinal flow of an electrolytic fluid along the semipermeable membrane of the filter and a transverse flow of the electrolytic fluid through the semipermeable membrane of the filter, an integral of the change in conductivity is determined and compared with a preselected threshold value, it being ascertained that there is an incorrectly functioning state of the filter if the integral is less than the preselected threshold value.

17. The method according to claim 13, wherein it is concluded that there is an incorrectly functioning state of the filter if a change in the conductivity from the base value is not measured.

18. The method according to claim 12, wherein the electrolytic fluid is dialyzing fluid or permeate.

19. The method according to claim 12, wherein the filter is a capillary filter which comprises a bundle of hollow fibers.

20. The method according to claim 12, wherein the filter is a pyrogen filter for filtering dialyzing fluid for an extracorporeal blood treatment apparatus.

* * * * *